(12) United States Patent
Guggenberger et al.

(10) Patent No.: US 10,492,857 B2
(45) Date of Patent: Dec. 3, 2019

(54) DEPLOYMENT CONTROL APPARATUS FOR A CATHETER WITH A DEPLOYABLE ARRAY

(71) Applicant: Boston Scientific Scimed Inc., Maple Grove, MN (US)

(72) Inventors: Kurt E. Guggenberger, North Andover, MA (US); William Quinn, Swampscott, MA (US); Doron Harlev, Brookline, MA (US); Ian Collier, Newton, MA (US)

(73) Assignee: Boston Scientific Scimed Inc, Maple Grove, MN (US)

( * ) Notice: Subject to any disclaimer, the term of this patent is extended or adjusted under 35 U.S.C. 154(b) by 682 days.

(21) Appl. No.: 15/228,786

(22) Filed: Aug. 4, 2016

(65) Prior Publication Data

US 2017/0035311 A1    Feb. 9, 2017

Related U.S. Application Data (60) Provisional application No. 62/202,051, filed on Aug. 6, 2015.

(51) Int. Cl.
*A61B 5/04* (2006.01)
*A61N 1/00* (2006.01)
(Continued)

(52) U.S. Cl.
CPC ........ *A61B 18/1492* (2013.01); *A61B 5/0422* (2013.01); *A61B 5/6858* (2013.01);
(Continued)

(58) Field of Classification Search
USPC ........ 600/372–375, 377, 381, 393, 466–470, 600/481, 508–509; 604/95.04, 523–530,
(Continued)

(56) References Cited

U.S. PATENT DOCUMENTS 5,026,377 A  *  6/1991  Burton ...................... A61F 2/82
                                                                606/108
5,311,858 A  *  5/1994  Adair ................... A61B 17/221
                                                                600/106

(Continued)

FOREIGN PATENT DOCUMENTS

EP          1902746 B1    6/2009
EP          1895886 B1    3/2010
(Continued)

*Primary Examiner* — Joseph A Stoklosa
*Assistant Examiner* — Brian M Antiskay
(74) *Attorney, Agent, or Firm* — Faegre Baker Daniels LLP (57) ABSTRACT

A deployment control apparatus to control deployment of an array at an end of a catheter includes a pair of walls, a slider assembly, and a deployment shaft. The walls project from a first surface of the interior of a handle. The slider assembly includes a rigid body, an elastomeric element, a tab, and a knob. The elastomeric element is connected to the rigid body and at least partially disposed between the walls to frictionally engage with a surface of each wall. The knob is connected to the rigid body and is configured to maintain the elastomeric element between the walls. The deployment shaft connects the rigid body to the array, wherein a force applied to the knob sufficient to overcome the frictional engagement between the elastomeric element and the surface of each wall causes movement of the slider assembly and the deployment shaft to control deployment of the array.

20 Claims, 11 Drawing Sheets

(51) Int. Cl.
  *A61B 18/14* (2006.01)
  *A61B 5/042* (2006.01)
  *A61B 5/00* (2006.01)
  *A61B 18/00* (2006.01)
(52) U.S. Cl.
  CPC .............. *A61B 2018/00267* (2013.01); *A61B 2018/00839* (2013.01)
(58) Field of Classification Search
  USPC ................... 604/536; 606/32, 41, 250–252; 607/115–116, 119, 122–123, 127–131
  See application file for complete search history.

(56) References Cited

U.S. PATENT DOCUMENTS

| | | | |
|---|---|---|---|
| 5,327,905 A | 7/1994 | Avitall | |
| 5,364,351 A | 11/1994 | Heinzelman et al. | |
| 5,456,664 A | 10/1995 | Heinzelman et al. | |
| 5,471,982 A | 12/1995 | Edwards et al. | |
| 5,681,280 A | 10/1997 | Rusk et al. | |
| 6,029,091 A | 2/2000 | de la Rama et al. | |
| 6,254,633 B1* | 7/2001 | Pinchuk | A61B 17/12022 606/200 |
| 6,461,356 B1 | 10/2002 | Patterson | |
| 7,269,453 B2 | 9/2007 | Mogul | |
| 7,465,288 B2 | 12/2008 | Dudney et al. | |
| 8,348,888 B2 | 1/2013 | Selkee | |
| 8,430,901 B2* | 4/2013 | Gilson | A61F 2/01 606/200 |
| 8,447,377 B2 | 5/2013 | Harlev et al. | |
| 8,460,237 B2 | 6/2013 | Schultz | |
| 8,480,658 B1 | 7/2013 | Nakao | |
| 8,518,035 B2* | 8/2013 | Ducharme | A61B 18/1482 606/39 |
| 8,523,808 B2 | 9/2013 | Selkee | |
| 8,617,087 B2 | 12/2013 | Schultz | |
| 8,696,620 B2 | 4/2014 | Tegg | |
| 8,747,351 B2* | 6/2014 | Schultz | A61B 5/04 604/95.04 |
| 8,771,267 B2 | 7/2014 | Kunis et al. | |
| 8,808,345 B2 | 8/2014 | Clark et al. | |
| 8,956,322 B2 | 2/2015 | Selkee | |
| 9,101,269 B2 | 8/2015 | Selkee | |
| 2009/0024137 A1* | 1/2009 | Chuter | A61F 2/95 606/108 |
| 2012/0209303 A1* | 8/2012 | Frankhouser | A61B 10/025 606/169 |
| 2013/0197481 A1* | 8/2013 | Guo | A61M 25/0012 604/527 |
| 2015/0374475 A1* | 12/2015 | McLawhorn | A61B 17/0057 606/151 |

FOREIGN PATENT DOCUMENTS

| | | |
|---|---|---|
| EP | 2204208 A2 | 7/2010 |
| EP | 2289592 B1 | 10/2012 |
| EP | 2308540 B1 | 4/2014 |
| EP | 1833398 B1 | 7/2014 |
| EP | 2543409 B1 | 5/2015 |

\* cited by examiner

Fig. 11D

DEPLOYMENT CONTROL APPARATUS FOR A CATHETER WITH A DEPLOYABLE ARRAY

CROSS-REFERENCE TO RELATED APPLICATION

This application claims priority to Provisional Application No. 62/202,051, filed Aug. 6, 2015, which is herein incorporated by reference in its entirety.

TECHNICAL FIELD

The present invention relates to medical catheters including deployable arrays for use inside a body. More specifically, the invention relates to devices and methods for controlling deployment of the array inside the body.

BACKGROUND

Cardiac arrhythmias may lead to heart disease and death. Arrhythmias may be treated by medication, implantable devices, or by the ablation of specific heart tissue found to be causing arrhythmia. Ablation may be performed by a number of techniques, including the local application of energy, for example, radio frequency energy, or by the application of cryogenic temperatures to the site of the problem tissue.

The specific heart tissue responsible for arrhythmia in a patient may be identified by moving a mapping catheter having one or more electrodes around the interior of the heart and measuring cardiac signals to sense changes in the electrical fields. A map of the electrical conductivity of the heart may be formed from the measurements to identify abnormalities which may be candidates for ablation. Some mapping catheters are designed such that the electrodes may physically contact the heart wall, including flexible designs that are inserted in a compact form and later deployed into a basket-like array. Such an array is deployed after entrance into the heart, and undeployed upon completion of the mapping and prior to removal from the heart.

In addition to cardiac mapping catheters, other medical catheters, such as endoscopic devices, may also include deployable devices, or arrays, for use within the body. There is a continuing need to improve the control of the deployment of such devices.

SUMMARY

Example 1 is a deployment control apparatus substantially contained within a handle at one end of a catheter to control deployment of an array at another end of the catheter. The deployment control apparatus includes a pair of walls, a slider assembly, and a deployment shaft. The walls project from a first surface of the interior of the handle. The walls are disposed on opposite sides of a slot extending along a portion of the handle between the interior of the handle and an exterior of the handle. The slider assembly includes a rigid body, an elastomeric element, a tab, and a knob. The elastomeric element is connected to the rigid body and at least partially disposed between the walls, wherein the elastomeric element frictionally engages with a surface of each wall. The tab is connected to the rigid body and projects from the rigid body and through the slot to the exterior of the handle. The knob is connected to the tab at the exterior of the handle, wherein the knob is configured to maintain the elastomeric element between the walls. The deployment shaft connects the rigid body to the array, wherein a force applied to the knob sufficient to overcome the frictional engagement between the elastomeric element and the surface of each wall causes movement of the slider assembly and the deployment shaft to control deployment of the array.

In Example 2, the apparatus of Example 1, wherein the frictional engagement between the elastomeric element and the surface of each wall prevents changes in the deployment of the array by means other than the deployment control apparatus.

In Example 3, the apparatus of either of Examples 1 or 2, wherein the slider assembly further includes a screw disposed through the elastomeric element and threadedly engaged with the rigid body to connect the elastomeric element to the rigid body.

In Example 4, the apparatus of Example 3, wherein increasing engagement of the screw with the rigid body compresses the elastomeric element toward the rigid body and increases a force of the elastomeric element toward the surface of each wall, thereby increasing the frictional engagement between the elastomeric element and the surface of each wall.

In Example 5, the apparatus of any of Examples 1-4, wherein the deployment control apparatus further includes a first rigid tube connected to interior of the handle, and a second rigid tube connected to the rigid body and configured to be in a telescoping arrangement with the first tube, wherein the deployment shaft extends through the first tube and the second tube.

In Example 6, the apparatus of any of Examples 1-5, wherein the walls extend from the first surface of the interior of the handle, and connect to a second surface of the interior of the handle opposite the first surface.

In Example 7, the apparatus of any of Examples 1-6, wherein the deployment shaft includes a braided polymeric tube.

In Example 8, the apparatus of any of Examples 1-7, wherein the rigid body includes a molded polymer, the tab includes a sheet of metal, and the tab is connected to the rigid body by overmolding a portion of the sheet of metal with the molded polymer.

In Example 9, the apparatus of any of Examples 1-8, wherein the walls are integrally formed with the handle.

Example 10 is a catheter including an elongate catheter body, an array, a handle, and a deployment control mechanism. The elongate catheter body extends from a proximal end to a distal end. The array is connected to the distal end of the catheter body. The array is continuously configurable between an undeployed configuration and a fully-deployed configuration. The handle is connected to the proximal end of the catheter body. The handle includes a slot extending along a portion of the handle between an interior of the handle and an exterior of the handle. The deployment control mechanism includes a pair of walls, a slider assembly, and a deployment shaft. The walls project from a first surface of the interior of the handle. The walls are disposed on opposite sides of the slot. The slider assembly includes a rigid body, an elastomeric element, a tab, and a knob. The elastomeric element is connected to the rigid body and at least partially disposed within a gap formed between the walls, wherein the elastomeric element frictionally engages with a surface of each wall. The tab is connected to the rigid body and projects from the rigid body and through the slot to the exterior of the handle. The knob is connected to the tab at the exterior of the handle, wherein the knob is configured to maintain the elastomeric element within the gap between the pair of walls. The deployment shaft connects the rigid body to the array, wherein a force applied to the knob sufficient to overcome the frictional engagement between the elastomeric element and the surface of each wall causes movement of the slider assembly and changes the configuration of the array.

In Example 11, the catheter of Example 10, wherein the array includes stiffening elements that produce a force biasing the array toward the undeployed configuration, and the frictional engagement between the elastomeric element and the surface of each wall is sufficient to prevent changes in the configuration array caused by the biasing force.

In Example 12, the catheter of either of Examples 10 or 11, wherein the slider assembly further includes a screw disposed through the elastomeric element and threadedly engaged with the rigid body to connect the elastomeric element to the rigid body, wherein increasing engagement of the screw with the rigid body compresses the elastomeric element toward the rigid body and increases a force of the elastomeric element toward the surface of each wall, thereby increasing the frictional engagement between the elastomeric element and the surface of each wall.

In Example 13, the catheter of any of Examples 10-12, wherein the deployment control mechanism further includes a first rigid tube connected to interior of the handle, and a second rigid tube connected to the rigid body distal of the first rigid tube and configured to be in a telescoping arrangement with the first rigid tube, wherein the deployment shaft extends through the first rigid tube and the second rigid tube.

In Example 14, the catheter of any of Examples 10-13, wherein the walls extend from the first surface of the interior of the handle and connect to a second surface of the interior of the handle opposite the first surface.

In Example 15, the catheter of any of Examples 10-14, wherein the walls are parallel to each other and to the slot.

In Example 16, the catheter of any of Examples 10-15, wherein the walls are symmetrically disposed on opposite sides of the slot.

In Example 17, the catheter of any of Examples 10-14, wherein the gap formed between the walls at a distal end of the walls is greater than the gap at a proximal end, wherein the force applied to the knob sufficient to overcome the frictional engagement between the elastomeric element and the surface of each wall increases as the deployment control mechanism changes the array from the undeployed configuration, to the partially-deployed configuration, to the nominally-deployed configuration, and to the fully-deployed configuration.

In Example 19, the catheter of any of Examples 10-14, wherein the gap formed between the walls is greater at a segment between a distal end of the walls and the proximal end of the walls, the segment corresponding to the nominally-deployed configuration, than at the distal end of the walls and the proximal end of the walls, wherein the force applied to the knob sufficient to overcome the frictional engagement between the elastomeric element and the surface of each wall decreases as the deployment control mechanism changes the array from the partially-deployed configuration to the nominally-deployed configuration, and increases as the deployment control mechanism changes the array from the nominally-deployed configuration to the fully-deployed configuration.

In Example 20, the catheter of any of Examples 10-19, wherein the catheter is a cardiac mapping catheter and the array is an electrode array While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

Catheters embodying the present invention may be employed in cardiac mapping catheters as described in "CARDIAC MAPPING CATHETER" (U.S. Pat. No. 8,447,377, issued May 21, 2013), hereby incorporated by reference in its entirety. Such catheters typically have several flexible splines forming an array, each spline including a plurality of electrodes. Catheter embodiments of the present invention include a deployment control mechanism that permits adjustment of the array between an undeployed state and a continuous range of deployed states.

Figure 1:
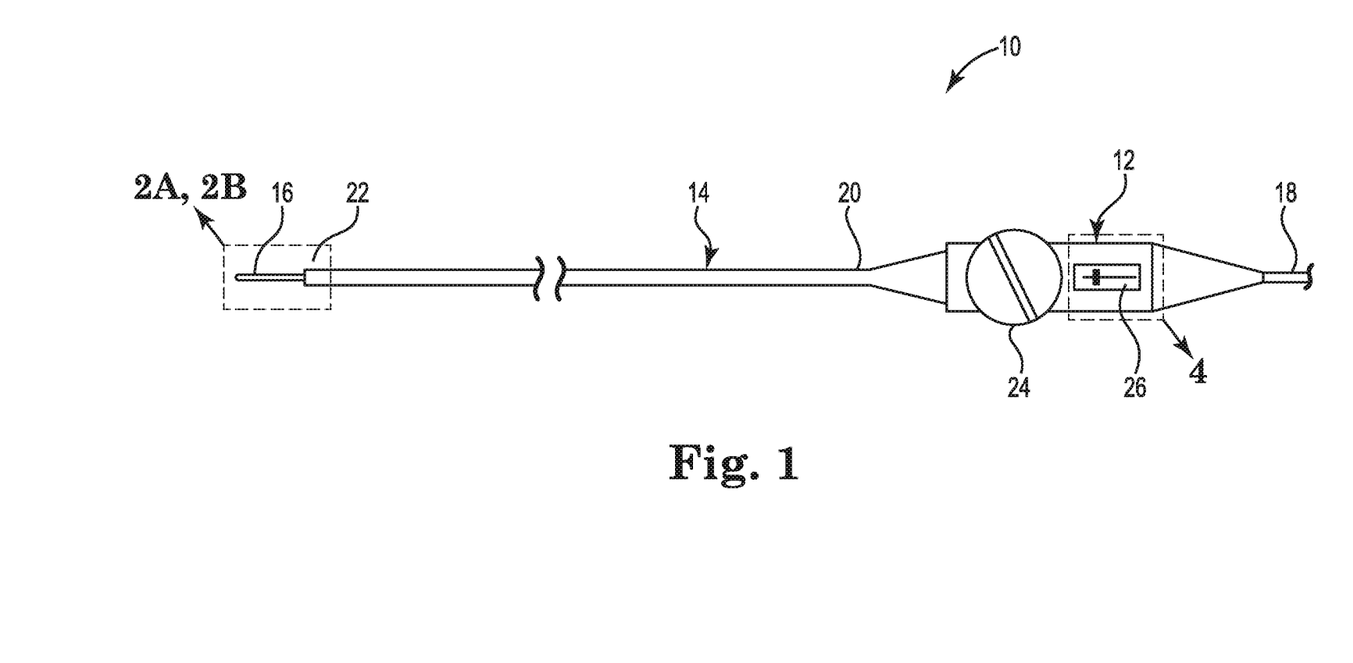
FIG. 1 is a schematic view of a cardiac mapping catheter suitable for use with embodiments of the present invention.

FIG. 1 provides an illustrative but non-limiting example of a cardiac mapping catheter 10 including an embodiment of a deployment control mechanism. As shown in FIG. 1, the cardiac mapping catheter 10 may include a handle 12, an elongate catheter body 14, an electrode assembly 16, and an electrical connection 18. The catheter body 14 may extend from a proximal end 20 to a distal end 22. The electrode array 16 may project from the distal end 22 of the catheter body 14. The catheter body 14 may be connected at the proximal end 20 to the handle 12. The electrical connection 18 may extend from the handle 12 to a mapping data recording and analysis system (not shown). The handle 12 may include an articulation control mechanism 24 and a deployment control mechanism 26.

The articulation control mechanism 24 may control bending of the distal end 22 of the catheter body 14 by way of one or more articulation control elements, for example wires (not shown) extending from the articulation control 24 to the distal end 22 by way of one or more lumens (not shown) extending through the catheter body 14 from the proximal end 20 to the distal end 22. Bending the distal end 22 provides for flexibility in maneuvering the electrode array 16 within a patient's heart.

The deployment control mechanism 26 may include a deployment shaft 28 (shown in FIGS. 2B and 5) to deploy the electrode array 16. The deployment shaft 28 may extend from handle 12 to the electrode array 16 by way of one of the lumens extending through the catheter body 14. The lumens may also include a set of electrical conductors (not shown) extending from the electrode array 16 to handle 12 to connect the electrode array 16 to the mapping data recording and analysis system.

Figure 2A:
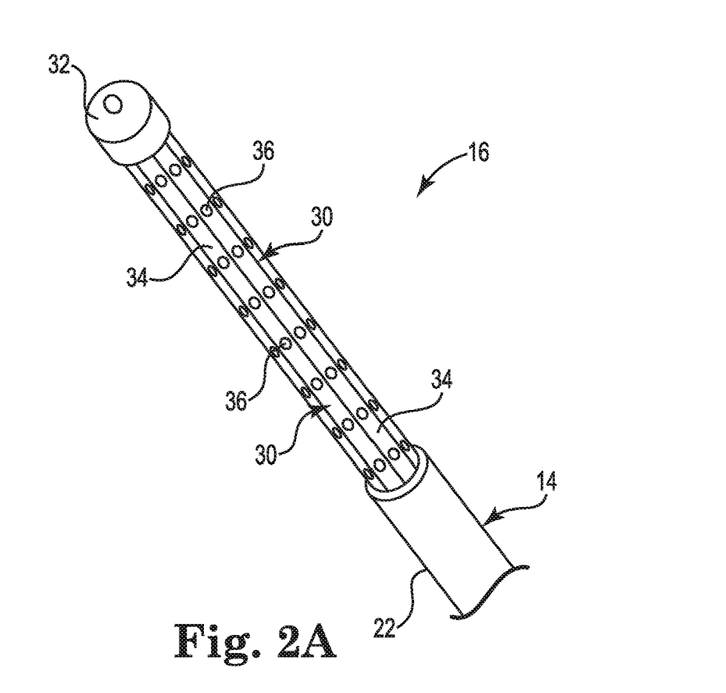
FIGS. 2A and 2B are partial perspective views showing a distal end of the mapping catheter of FIG. 1.
Figure 2B:
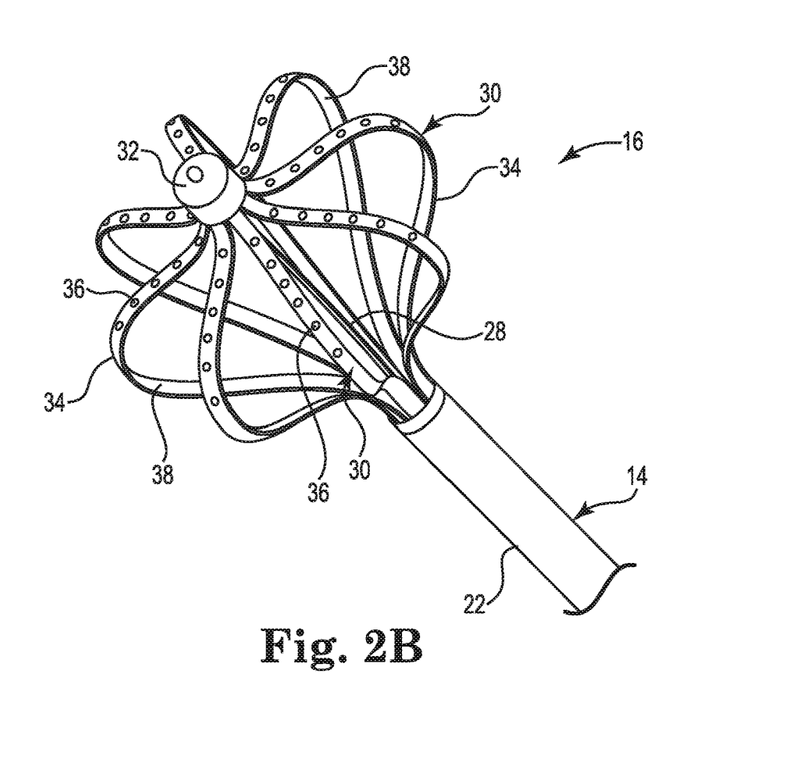

FIGS. 2A and 2B are partial perspective views showing the electrode array 16 and the distal end 22 of the cardiac mapping catheter 10 of FIG. 1. FIG. 2A shows the electrode array 16 undeployed in a radially retracted state. FIG. 2B shows the electrode array 16 deployed in a radially extended state. As shown in FIGS. 2A and 2B, the electrode array 16 may include a plurality of splines 30 and an end cap 32. Each of the plurality of splines 30 may extend between the distal end 22 and the end cap 32. Each of the splines 30 may include a flexible polymer substrate 34 and a plurality of electrodes 36. In some embodiments, the flexible polymer substrate 34 may include a stiffening element 38. The stiffening element 38 may be, for example, a layer of nitinol. The stiffening element 38 may produce a force in each of the splines 30 that biases the electrode array 16 toward the undeployed state or configuration. In the exemplary embodiment shown in FIGS. 2A and 2B, there are eight splines 30, each including eight electrodes 36, for a total of sixty-four electrodes in the electrode array 16.

As shown in FIG. 2B, the deployment shaft 28 may extend from the end cap 32 and into the catheter body 14 at the distal end 22. The deployment shaft 28 may be a braided polyimide shaft connecting end cap 32 to the deployment control mechanism 26 (see FIG. 5) such that actuation of the deployment control mechanism 26 may cause the deployment shaft 28 to move in the proximal direction and pull the end cap 32 in the proximal direction. Movement of the end cap 32 in the proximal direction may cause the plurality of splines 30 to flex radially outward and deploy the electrode array 16 as shown in FIG. 2B.

In some embodiments, the end cap 32 may also be an electrode for cardiac stimulation or tissue ablation. In other embodiments, the end cap 32 may contain a magnetic sensor for use in determining the location of the electrode array 16 within the body. In these embodiments, one or more conductors 40 (see FIG. 5) may extend from the end cap 32 to the handle 12 by way of a lumen within the deployment shaft 28 to connect the end cap 32 to the mapping data recording and analysis system.

In use, the cardiac mapping catheter 10 may be inserted into a patient's vasculature with the electrode array 16 in the undeployed, radially retracted state shown in FIG. 2A and advanced to the interior of the patient's heart. Once within the heart, the electrode array 16 may be deployed by deployment control 26 as described above into the radially extended state shown in FIG. 2B to sense the cardiac signals within the heart. The sensed cardiac signals may be transmitted to the mapping data recording and analysis system by way of the set of electrical conductors extending through the catheter body 14 from the electrode array 16 to the handle 12, and the electrical connection 18. In some embodiments, the electrode array 16 may be deployed in into a less-radially extended state for use in, for example, the pulmonary vein. The deployment control mechanism 26 provides for adjustment of the electrode array 16 between the undeployed state and a continuous range of such deployed states. Once the cardiac mapping is completed, the electrode array 16 may be undeployed into the radially retracted state and withdrawn from the patient.

Figure 3A:
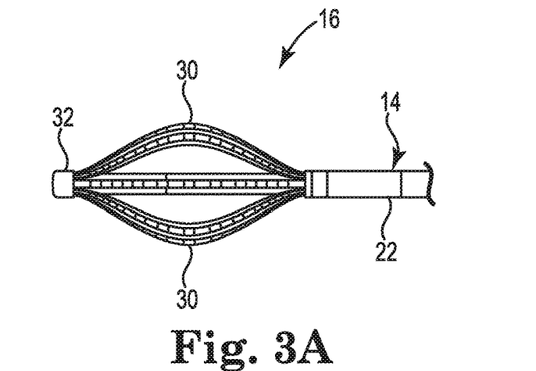
FIGS. 3A-3C are side views showing exemplary deployment configurations of the mapping catheter of FIGS. 2A and 2B.
Figure 3B:
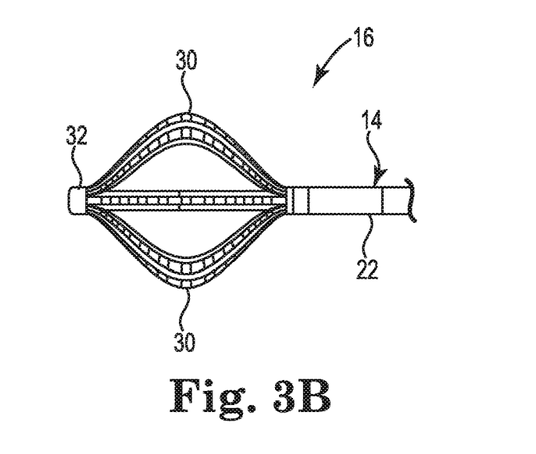
Figure 3C:
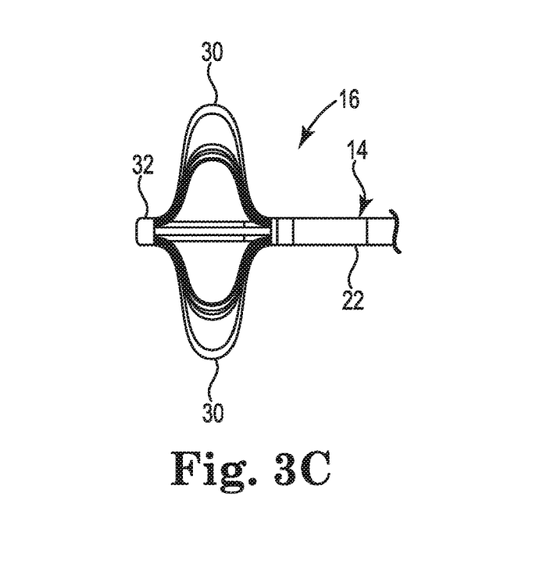

FIGS. 3A-3C are side views showing various exemplary deployment configurations of the electrode array 16 of the cardiac mapping catheter 10. FIG. 3A shows the electrode array 16 in a partially-deployed configuration. The partially-deployed configuration may be employed in mapping smaller structures, for example, the pulmonary vein. The partially-deployed configuration may be deployed from the undeployed configuration by movement of the deployment control mechanism 26 to cause the deployment shaft 28 to move in the proximal direction, thus pulling the end cap 32 in the proximal direction. FIG. 3B shows the electrode array 16 in a nominally-deployed configuration. The nominally-deployed configuration may be employed, for example, in most instances when mapping within the heart. The nominally-deployed configuration may be deployed by movement of the deployment control mechanism 26 to cause the deployment shaft 28 to move farther in the proximal direction than for the partially-deployed configuration, thus pulling the end cap 32 farther in the proximal direction. FIG. 3C shows the electrode array 16 in a fully-deployed configuration. The fully-deployed configuration may be employed in some instances when mapping within the heart. The fully-deployed configuration may be deployed by movement of the deployment control mechanism 26 to cause the deployment shaft 28 to move farther in the proximal direction than for the nominally-deployed configuration, thus pulling the end cap 32 even farther in the proximal direction.

The descriptions of partially-deployed, nominally-deployed, and fully-deployed configurations are intended to be relative descriptions. It is understood that embodiments permit the electrode array 16 to be adjusted along a continuous spectrum from the undeployed configuration to the fully-deployed configuration. This feature permits the cardiac mapping catheter 10 to function in a wide variety of applications. In addition, because patients vary in size, the size of their heart and veins will also vary. The continuous adjustability of the electrode array 16 also permits the cardiac mapping catheter 10 to function well for a wide variety of patients.

Figure 4:
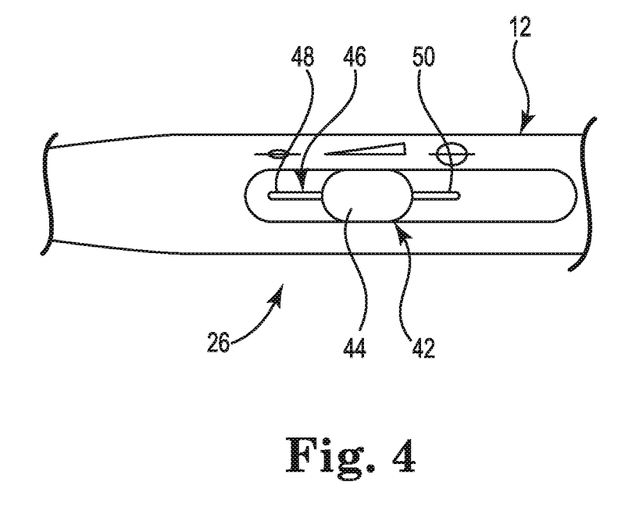
FIG. 4 is an exterior view of the cardiac mapping catheter handle showing a portion of the deployment control mechanism.

FIG. 4 is an exterior view of the cardiac mapping catheter handle 12 showing a portion of the deployment control mechanism 26. The deployment control mechanism 26 includes a slider assembly 42, of which only a knob 44 is visible on the exterior of handle 12. As shown in FIG. 4, the handle 12 further includes a slot 46. The slot 46 extends along a portion of the handle 12 from a distal slot end 48 to a proximal slot end 50. The slot 46 also extends between the exterior of the handle 12 and an interior of handle 12, as described below in reference to FIGS. 6 and 7. The electrode array 16 may be deployed from the undeployed configuration to the fully-deployed configuration, and any configuration in between, by applying force to the knob 44 in the proximal direction to move the knob 44 from the distal slot end 48 toward the proximal slot end 50. Applying a force to the knob 44 in the distal direction reverses the deployment of the electrode 16.

Figure 5:
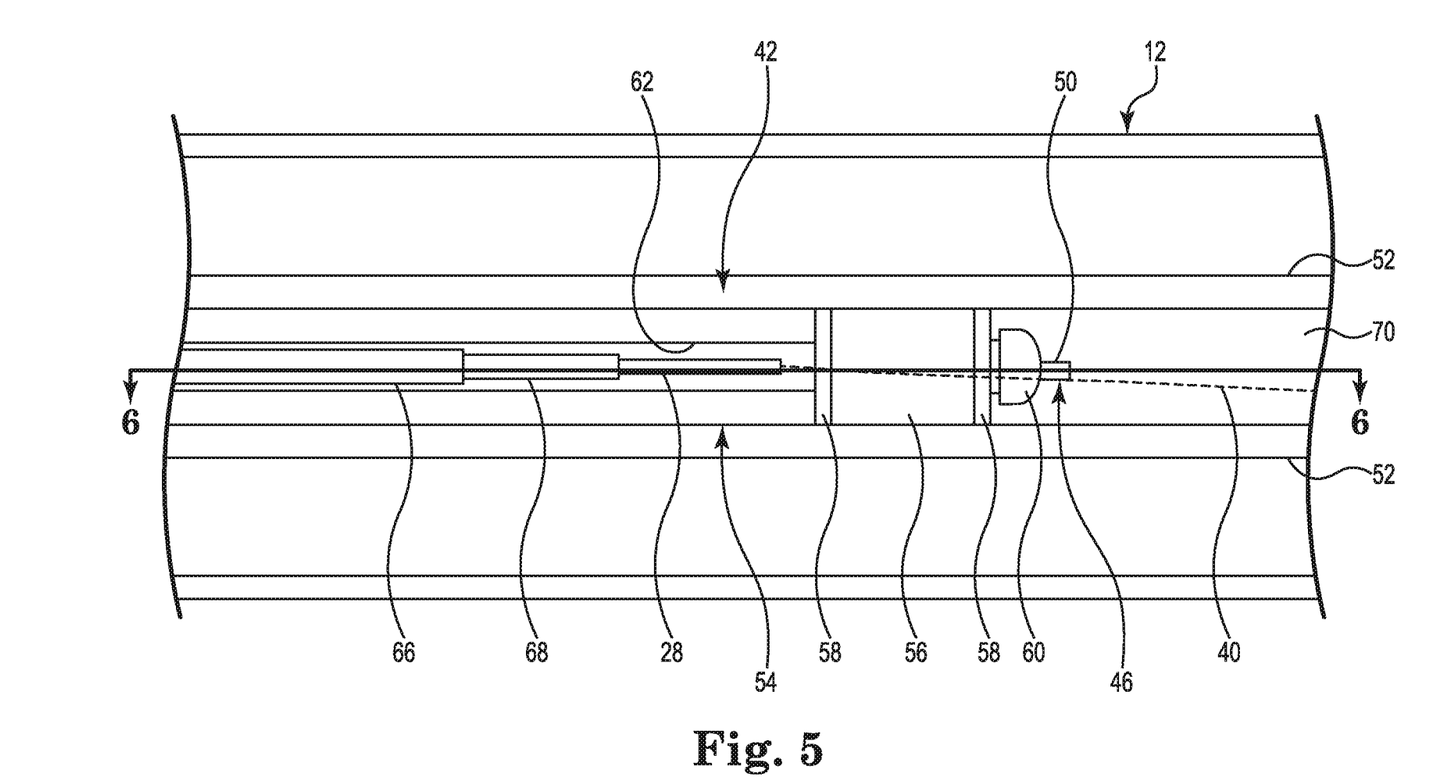
FIG. 5 is an interior view of the cardiac mapping catheter handle showing another portion of the deployment control mechanism.

FIG. 5 is an interior view of the cardiac mapping catheter handle 12 showing another portion of the deployment control mechanism 26. As shown in FIG. 5, the deployment control mechanism 26 further includes a pair of walls 52. The walls 52 are rigid and extend from a first surface 70 of the interior of the handle 12. In some embodiments, the walls 52 are integrally formed with the handle 12. The walls 52 are disposed on opposite sides of the slot 46. In the embodiment shown in FIG. 5, the walls 52 are parallel to each other. The slider assembly 40 may further include a rigid body 54, an elastomeric element 56, a pair of washers 58, and screw 60. The rigid body 54 may include a recess 62 running along at least a portion of its length (shown more clearly in FIGS. 6 and 7). The rigid body 54 may be made of a hard polymer, for example, a glass filled polycarbonate, nylon, polyetherimide, polyether ether ketone, or acrylonitrile butadiene styrene. The elastomeric element 56 may be cylindrical in shape. The elastomeric element 56 may be made of a soft polymer, for example, polysiloxane or polyurethane. In one embodiment, the washers 58 may be made of nylon. In other embodiments, the washers 58 may be made of other polymeric or non-polymeric materials having similar mechanical and chemical characteristics as nylon. The screw 60 includes a threaded shaft and may be made of stainless steel. In the embodiment shown in FIG. 5, the deployment control mechanism 26 further includes a first rigid tube 66 and a second rigid tube 68. The first rigid tube 66 and the second rigid tube 68 may be made of stainless steel. In some embodiments, the first rigid tube 66 and the second rigid tube 68 may be made of sections of stainless steel hypo-tubes.

The washers 58 are disposed on axially opposite ends of the elastomeric element 56. The elastomeric element 56 and the washers 58 are connected to the rigid body 54 by the screw 60 as described below in reference to FIG. 6. Thus, one of the washers 58 is disposed between the elastomeric element 56 and the rigid body 54, and the other one of the washers 58 is disposed between the elastomeric element 58 and a head of the screw 60.

The first rigid tube 66 may be connected at its distal end to an interior surface of the handle 12 or to another component rigidly attached to the interior surface of the handle 12. The second rigid tube 68 may be connected at its proximal end to the rigid body 54 within the recess 62 by, for example, an adhesive. The first rigid tube 66 and the second rigid tube 68 have different diameters. The first rigid tube 66 and the second rigid tube 68 may be configured to be in a telescoping arrangement such that as the first rigid tube 66 and the second rigid tube 68 slide past each other, they continue to form a continuous lumen throughout the range of motion of the slider assembly 42 relative to the handle 12. The deployment shaft 28 extending from the electrode array 16 to handle 12 by way of one of the lumens extending through the catheter body 14 may extend through the first rigid tube 66 and the second rigid tube 68. A proximal end of the deployment shaft 28 may be connected to the rigid body 54 within the recess 62 by, for example, application of an adhesive.

The slider assembly 40 is disposed within handle 12 such that the elastomeric element 56 is at least partially disposed between the pair of walls 52. The elastomeric element 56 frictionally engages with a surface of each of the walls 52. The frictional engagement between the elastomeric element 56 and the walls 52 may be sufficient to prevent changes in the deployment configuration of the electrode array 16 caused by either the biasing force of the splines 30 as described above in reference to FIGS. 2A and 2B, or by a force of a beating heart against the splines during mapping. Thus, the deployment control mechanism 26 provides for adjustment of the electrode array 16 between the undeployed state and a continuous range of deployed states, and automatically holds the electrode array 16 in any deployment state.

Figure 6:
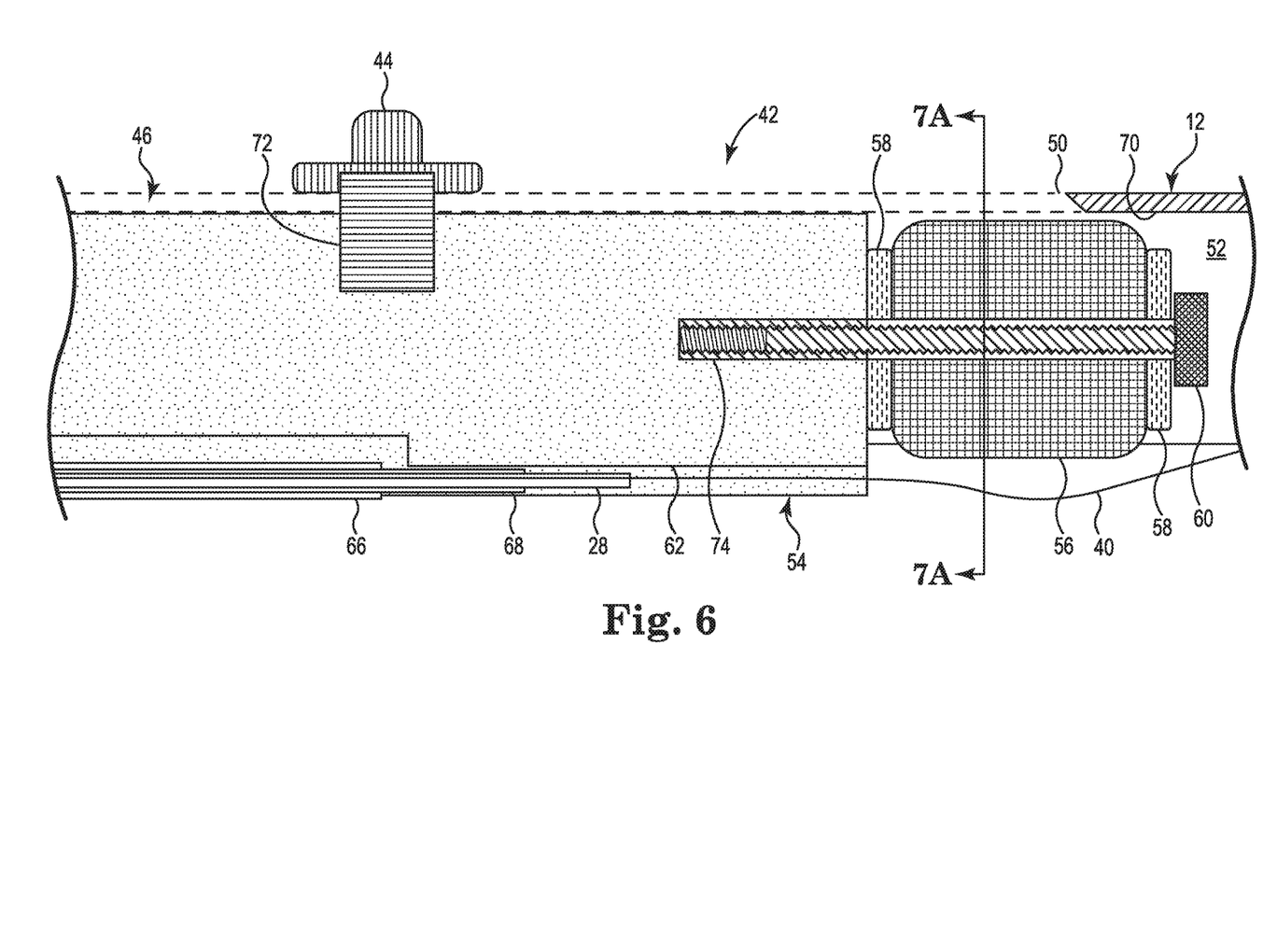
FIG. 6 is a schematic lengthwise cross-section of a portion of the deployment control mechanism.

FIG. 6 is a schematic lengthwise cross-section of a portion of the deployment control mechanism 26 shown in FIG. 5. As shown in FIG. 6, the slider assembly 42 further includes a tab 72 connecting the knob 44 to the rigid body 54. The tab 72 may be made of a sheet metal. The tab 72 may be attached to the rigid body 54 by, for example, over-molding. The tab 72 may be attached to the knob 44 by a snap fit after the tab 72 is inserted through the slot 46. As shown in FIG. 6, the rigid body 54 further includes a threaded hole 74. The screw 60 threadedly engages with the threaded hole 74 of the rigid body 54 to connect the elastomeric element 56 and the washers 58 to the rigid body 54.

The frictional engagement between the elastomeric element 56 and the walls 52 may be adjusted by the operation of screw 50. Increasing engagement of the screw 60 with the rigid body 54 compresses the elastomeric element 56 toward the rigid body 54. Compressing the elastomeric element 56 in this way tends to force the elastomeric element 56 to expand in directions perpendicular to the direction of compression. In the direction of the walls 52, this increases the frictional engagement between the elastomeric element 56 and the walls 52 because the elastomeric element 56 is constrained by walls 52. Conversely, reducing the engagement of the screw 60 with the rigid body 54 may reduce the frictional engagement between the elastomeric element 56 and the walls 52. In this way, the frictional engagement between the elastomeric element 56 and the walls 52 may be adjusted such that it is sufficient to prevent changes in the deployment configuration of the electrode array 16 caused by either the biasing force of the splines 30 or by a force of a beating heart against the splines during use, while ensuring that the frictional engagement is not so great as to make movement of the slider assembly difficult when intentionally changing the deployment configuration.

Figure 7:
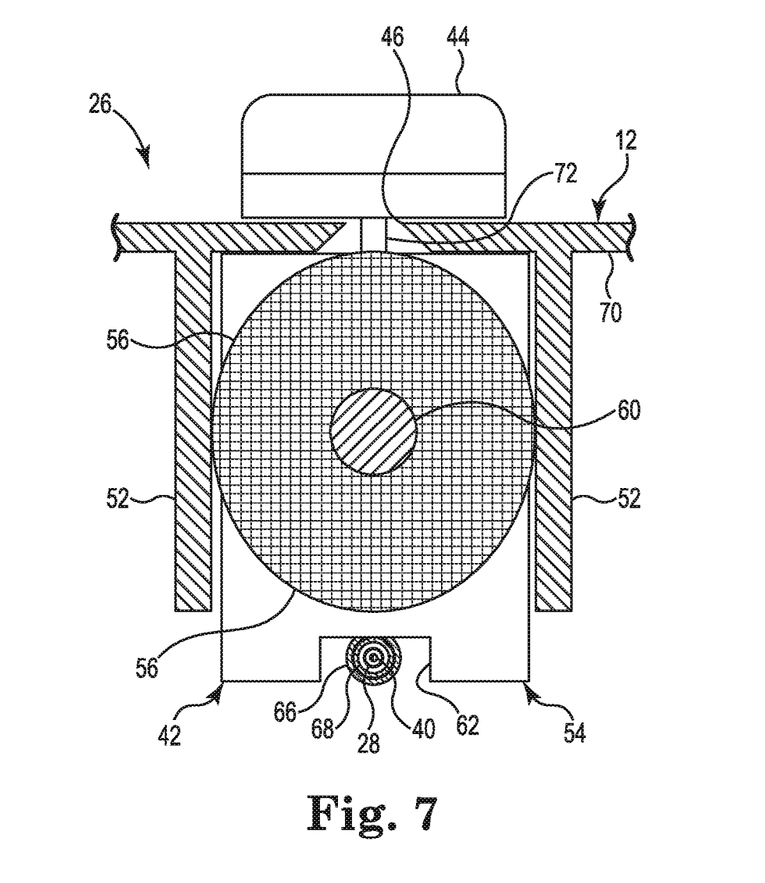
FIG. 7 is a schematic cross-section of the deployment control mechanism in a plane perpendicular to the cross-section of FIG. 6.

FIG. 7 is a schematic cross-section of the deployment control mechanism 26 in a plane perpendicular to the cross-section of FIG. 6. FIG. 7 illustrates the frictional engagement between the elastomeric element 56 and the walls 52. In the embodiment shown in FIG. 7, the walls 52 are integrally formed with the handle 12. The walls 52 are disposed on opposite sides of the slot 46. As shown in FIG. 7, the tab 72 extends through the slot 46, connecting the knob 44 to the rigid body 54. So configured, knob 44 maintains the elastomeric element 56 within the gap between the pair of walls 52. FIG. 7 shows the first rigid tube 66, the second rigid tube 68, the deployment shaft 28, and the conductor 44 within the recess 62. The conductor 44 is within the lumen of the deployment shaft 28. The deployment shaft 28 is arranged within lumens of both the first rigid tube 66 and the second rigid tube 68. As noted above in reference to FIG. 65, the first rigid tube 66 and the second rigid tube 68 are in a telescoping arrangement.

Figure 8:
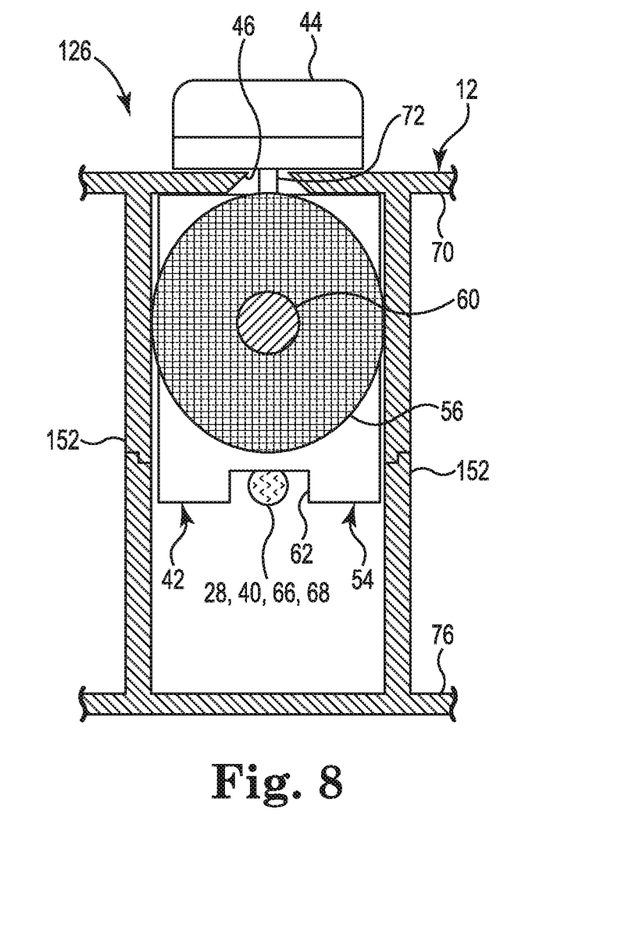
FIG. 8 is a schematic cross-section of another embodiment of the deployment control mechanism.

FIG. 8 is a schematic cross-section of another embodiment of the deployment control mechanism. FIG. 8 shows a deployment control mechanism 126. The deployment control mechanism 126 is identical to the deployment control mechanism 26 described above in reference to FIGS. 5-7, except that a pair of walls 152 extending from the first surface 70 of the interior of the handle and connecting to a second surface 76 of the interior of the handle replace the pair of walls 52. The second surface 76 is opposite of the first surface 70. Portions of each of the walls 152 may be integrally formed with two opposite halves of the handle 12. The walls 152 may be formed by assembly of the two halves to form handle 12, bringing the portions of each of the walls 152 together. In some embodiments, the portions of the walls 152 interlock such that the walls 152 form a continuous structure supported from the first surface 70 and the second surface 76.

Figure 9A:
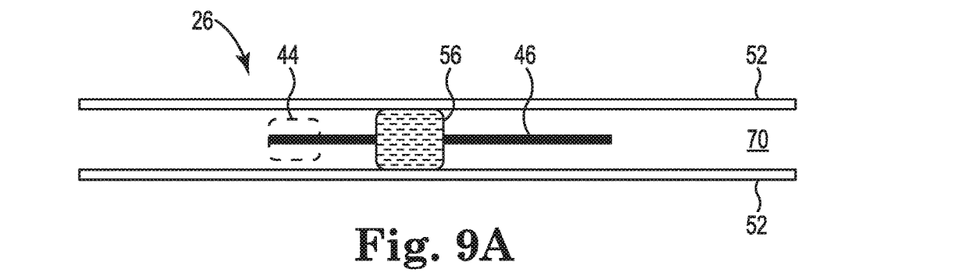
FIGS. 9A-9D are schematic views of the interior of the cardiac mapping catheter of FIGS. 5-7 showing the deployment control mechanism in positions corresponding to various deployment configurations.
Figure 9B:
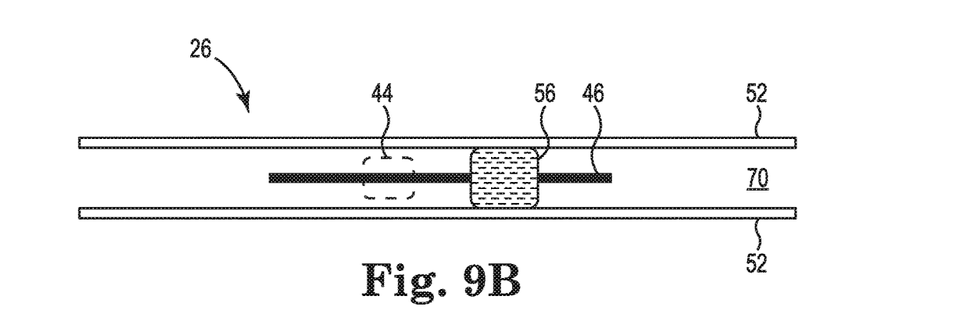
Figure 9C:
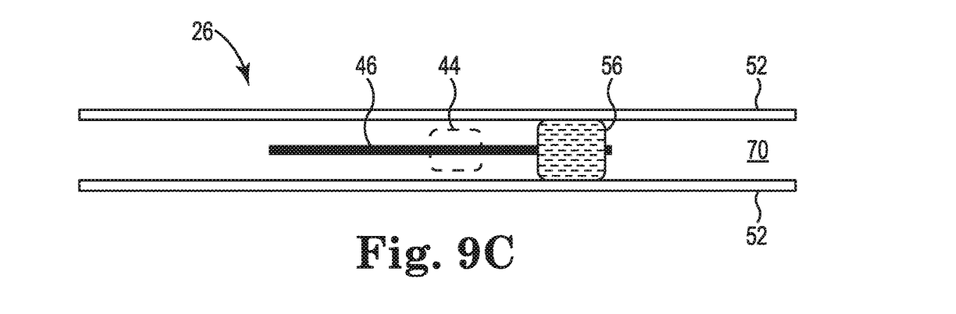
Figure 9D:
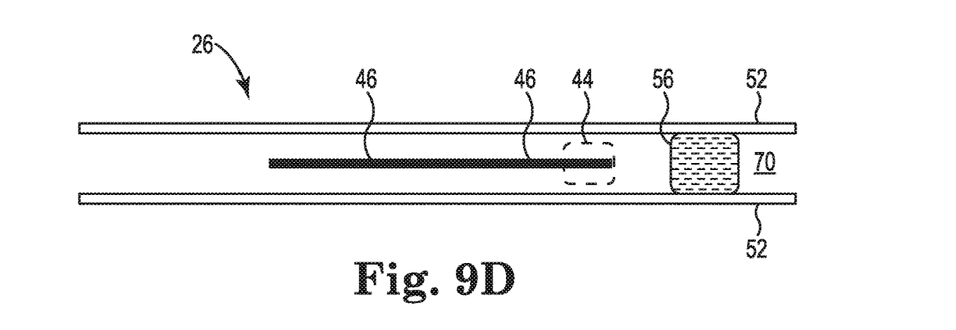

FIGS. 9A-9D are schematic views of the interior of the handle 12 of the cardiac mapping catheter of FIGS. 5-7 showing the deployment control mechanism 26 in positions corresponding to various deployment configurations as described above in reference to FIG. 4. FIGS. 9A-9D show the deployment mechanism 26 including the pair of walls 52, the elastomeric element 56, and the knob 44. Also shown is the slot 46. The remaining components of the deployment control mechanism 26 are omitted for clarity. The knob 44 at the exterior of the interior of the handle 12 is shown in outline. As noted above in reference to FIG. 5 and shown in FIGS. 9A-9D, the walls 52 are substantially parallel to each other. FIG. 9A shows the position of the deployment control mechanism 26 corresponding to the undeployed configuration of the electrode array 16 as shown in FIG. 2A. In this position, the knob 44 is at the distal end of the slot 46. FIG. 9B shows the position of the deployment control mechanism 26 corresponding to the partially-deployed configuration of the electrode array 16 as shown in FIG. 3A. In this position, the knob 44 is proximal from the distal end of the slot 46, but not to a midpoint of the slot 46. FIG. 9C shows the position of the deployment control mechanism 26 corresponding to the nominally-deployed configuration of the electrode array 16 as shown in FIG. 3B. In this position, the knob 44 is at the midpoint of the slot 46. FIG. 9D shows the position of the deployment control mechanism 26 corresponding to the fully-deployed configuration of the electrode array 16 as shown in FIG. 3C. In this position, the knob 44 is at the proximal end of the slot 46. In this embodiment, the force that must be applied to the knob 44 to overcome the frictional engagement between the elastomeric element 56 and the walls 52 is substantially the same when moving between any of the four configurations, or to any other configuration between any of the four configurations, because the gap between the walls 52 does not change along the length of the walls 52.

Figure 10A:
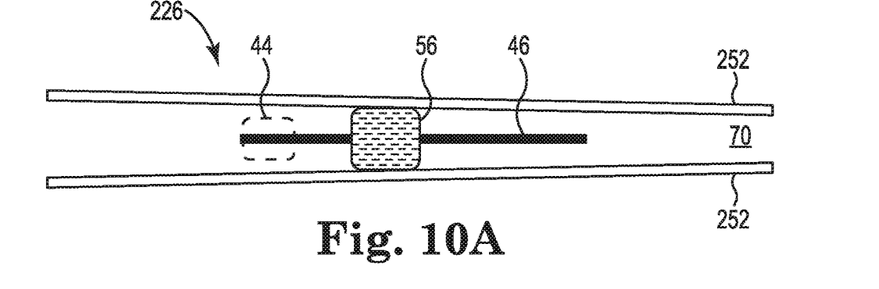
FIGS. 10A-10D are schematic views of an interior of another embodiment of the cardiac mapping catheter showing a deployment control mechanism in positions corresponding to various deployment configurations.
Figure 10B:
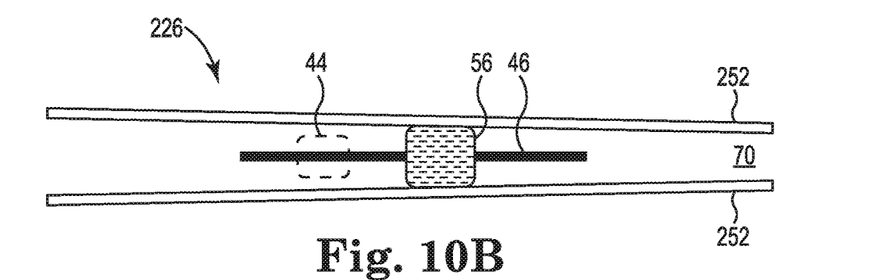
Figure 10C:
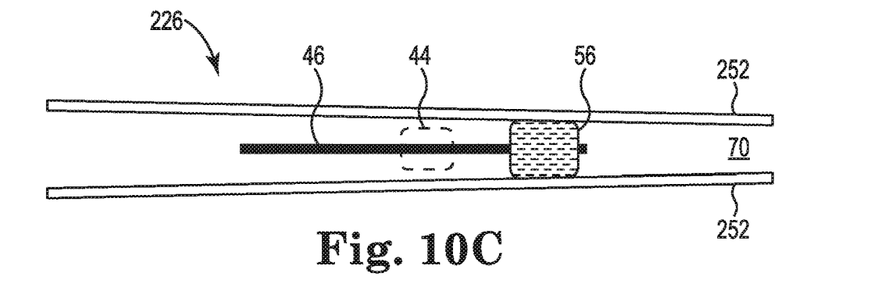
Figure 10D:
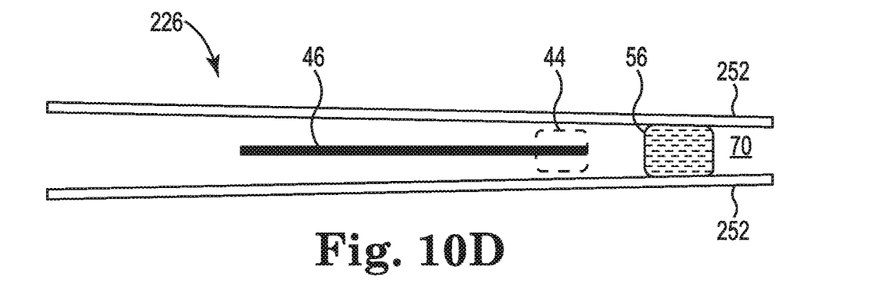

FIGS. 10A-10D are schematic views of an interior of another embodiment of the cardiac mapping catheter showing a deployment control mechanism 226 in positions corresponding to the various deployment configurations. The deployment control mechanism 226 is identical to the deployment control mechanism describe above in reference to FIGS. 9A-9D, except that the pair of walls 52 is replace by the pair of walls 252. The walls 252 are identical to the walls 52, except that the gap formed between the pair of walls 252 at a distal end is greater than the gap at the proximal end. FIG. 10A shows the position of the deployment control mechanism 226 corresponding to the undeployed configuration of the electrode array 16 with the knob 44 at the distal end of the slot 46. FIG. 10B shows the position of the deployment control mechanism 226 corresponding to the partially-deployed configuration of the electrode array 16 as shown in FIG. 3A with the knob 44 proximal from the distal end of the slot 46, but not to a midpoint of the slot 46. FIG. 10C shows the position of the deployment control mechanism 226 corresponding to the nominally-deployed configuration of the electrode array 16 as shown in FIG. 3B with the knob 44 at the midpoint of the slot 46. FIG. 10D shows the position of the deployment control mechanism 226 corresponding to the fully-deployed configuration of the electrode array 16 as shown in FIG. 3C with the knob 44 at the proximal end of the slot 46. In this embodiment, the force that must be applied to the knob 44 to overcome the frictional engagement between the elastomeric element 56 and the walls 252 increases as the deployment control mechanism 226 changes the electrode array 16 from the undeployed configuration, to the partially-deployed configuration, to the nominally-deployed configuration, and to the fully-deployed configuration. Thus, this embodiment may provide tactile feedback to assist the user in determining the deployment configuration of the electrode array 16. However, even with the varying frictional engagement over the range of deployment of the electrode array 16, the frictional engagement between the elastomeric element 56 and the walls 252 remains sufficient to prevent changes in the deployment configuration of the electrode array 16 caused by either the biasing force of the splines 30 or by a force of a beating heart against the splines during use.

Figure 11A:
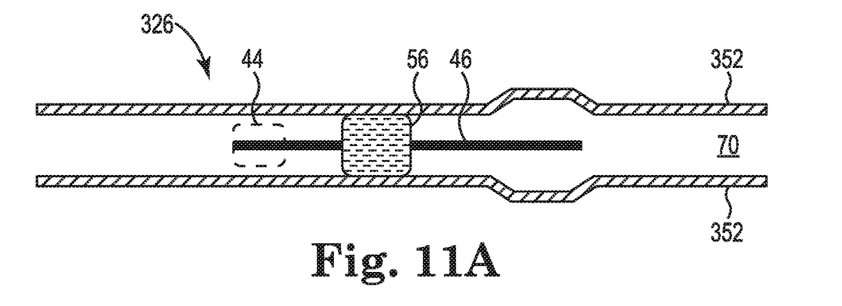
FIGS. 11A-11D are schematic views of an interior of yet another embodiment of the cardiac mapping catheter showing a deployment control mechanism in positions corresponding to various deployment configurations.
Figure 11B:
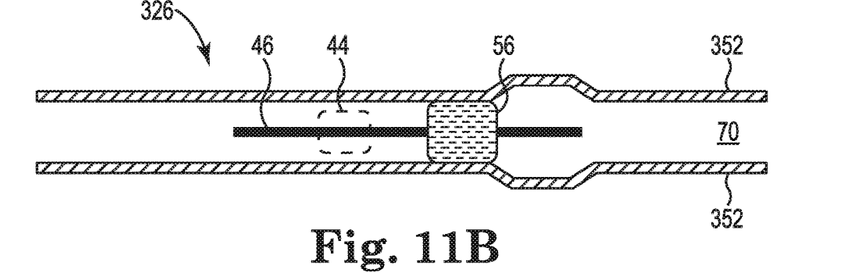
Figure 11C:
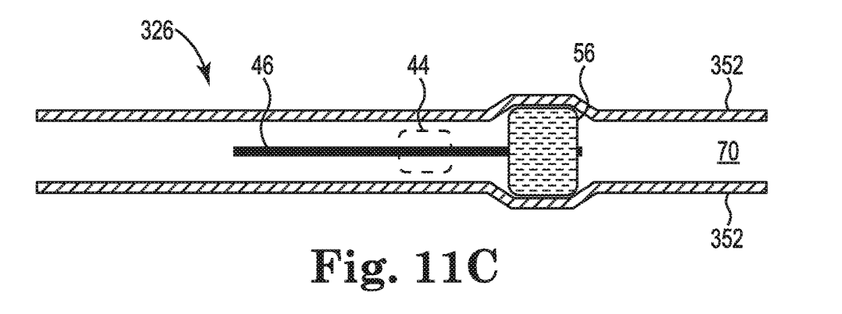
Figure 11D:
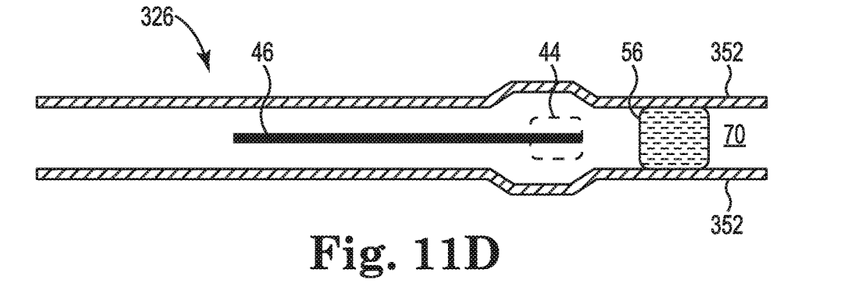

FIGS. 11A-11D are schematic views of an interior of another embodiment of the cardiac mapping catheter showing a deployment control mechanism 326 in positions corresponding to the various deployment configurations. The deployment control mechanism 326 is identical to the deployment control mechanism describe above in reference to FIGS. 9A-9D, except that the pair of walls 52 is replace by the pair of walls 352. The walls 352 are identical to the walls 52, except that the gap formed between the pair of walls 352 is greater at a segment between the distal end of the walls 352 and the proximal end of the walls 352, than the gap at the distal end of the walls 352 or the proximal end of the walls 352. FIG. 11A shows the position of the deployment control mechanism 326 corresponding to the undeployed configuration of the electrode array 16 with the knob 44 at the distal end of the slot 46. FIG. 11B shows the position of the deployment control mechanism 326 corresponding to the partially-deployed configuration of the electrode array 16 as shown in FIG. 3A with the knob 44 proximal from the distal end of the slot 46, but not to a midpoint of the slot 46. FIG. 11C shows the position of the deployment control mechanism 326 corresponding to the nominally-deployed configuration of the electrode array 16 as shown in FIG. 3B with the knob 44 at the midpoint of the slot 46. In this configuration, the elastomeric element 56 is disposed at the segment having the greater gap between the walls 352. FIG. 11D shows the position of the deployment control mechanism 326 corresponding to the fully-deployed configuration of the electrode array 16 as shown in FIG. 3C with the knob 44 at the proximal end of the slot 46. In this embodiment, the force that must be applied to the knob 44 to overcome the frictional engagement between the elastomeric element 56 and the walls 352 decreases as the deployment control mechanism 326 changes the electrode array 16 from the partially-deployed configuration to the nominally-deployed configuration. In contrast, the force that must be applied to the knob 44 to overcome the frictional engagement between the elastomeric element 56 and the walls 352 decreases as the deployment control mechanism 326 changes the electrode array 16 from the nominally-deployed configuration to the fully-deployed configuration. Thus, this embodiment may provide tactile feedback to assist the user in determining that the electrode array 16 is in the nominally-deployed configuration. As with the previously described embodiments, even with the varying frictional engagement over the range of deployment of the electrode array 16, the frictional engagement between the elastomeric element 56 and the walls 352 remains sufficient to prevent changes in the deployment configuration of the electrode array 16 caused by either the biasing force of the splines 30 or by a force of a beating heart against the splines during use.

The embodiments are described above for a cardiac mapping catheter. However, it is understood that embodiments may include other medical catheters, such as endoscopic devices, which may also include deployable devices, or arrays, for use within the body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A deployment control apparatus substantially contained within a handle at one end of a catheter to control deployment of an array at another end of the catheter, the deployment control apparatus comprising:
   a pair of walls projecting from a first surface of an interior of the handle, the walls disposed on opposite sides of a slot extending along a portion of the handle between the interior of the handle and an exterior of the handle;
   a slider assembly including:
      a rigid body;
      an elastomeric element connected to the rigid body and at least partially disposed between the walls, wherein the elastomeric element frictionally engages with a surface of each wall;
      a tab connected to the rigid body and projecting from the rigid body and through the slot to the exterior of the handle; and
      a knob connected to the tab at the exterior of the handle, wherein the knob is configured to maintain the elastomeric element between the walls;
   a deployment shaft connecting the rigid body to the array, wherein a force applied to the knob sufficient to overcome the frictional engagement between the elastomeric element and the surface of each wall causes movement of the slider assembly to control deployment of the array; and
   a screw disposed through the elastomeric element and threadly engaged with the rigid body to connect the elastomeric element to the rigid body.

2. The apparatus of claim 1, wherein the frictional engagement between the elastomeric element and the surface of each wall prevents changes in the deployment of the array by means other than the deployment control apparatus.

3. The apparatus of claim 1, wherein increasing engagement of the screw with the rigid body compresses the elastomeric element toward the rigid body and increases a force of the elastomeric element toward the surface of each wall, thereby increasing the frictional engagement between the elastomeric element and the surface of each wall.

4. The apparatus of claim 1, wherein the deployment control apparatus further includes:
   a first rigid tube connected to the interior of the handle; and
   a second rigid tube connected to the rigid body and configured to be in a telescoping arrangement with the first tube, wherein the deployment shaft extends through the first tube and the second tube.

5. The apparatus of claim 1, wherein the walls extend from the first surface of the interior of the handle, and connect to a second surface of the interior of the handle opposite the first surface.

6. The apparatus of claim 1, wherein the deployment shaft includes a braided polymeric tube.

7. The apparatus of claim 1, wherein the rigid body includes a molded polymer, the tab includes a sheet of metal, and the tab is connected to the rigid body by overmolding a portion of the sheet of metal with the molded polymer.

8. The apparatus of claim 1, wherein the walls are integrally formed with the handle.

9. A catheter comprising:
   an elongate catheter body extending from a proximal end to a distal end;
   an array connected to the distal end of the catheter body, the array continuously configurable between an undeployed configuration and a fully-deployed configuration; and
   a handle connected to the proximal end of the catheter body, the handle including a slot extending along a portion of the handle between an interior of the handle and an exterior of the handle; and
   a deployment control mechanism including:
      a pair of walls projecting from a first surface of the interior of the handle, the walls disposed on opposite sides of the slot;
      a slider assembly including:
         a rigid body;
         an elastomeric element connected to the rigid body and at least partially disposed within a gap formed between the walls, wherein the elastomeric element frictionally engages with a surface of each wall;
         a tab connected to the rigid body and projecting from the rigid body and through the slot to the exterior of the handle;
         a knob connected to the tab at the exterior of the handle, wherein the knob is configured to maintain the elastomeric element within the gap between the walls;
      a deployment shaft connecting the rigid body to the array, wherein a force applied to the knob sufficient to overcome the frictional engagement between the elastomeric element and the surface of each wall causes movement of the slider assembly and changes the configuration of the array; and
      a screw disposed through the elastomeric element and threadly engaged with the rigid body to connect the elastomeric element to the rigid body, wherein increasing engagement of the screw with the rigid body compresses the elastomeric element toward the rigid body and increases a force of the elastomeric element toward the surface of each wall, thereby increasing the frictional engagement between the elastomeric element and the surface of each wall.

10. The catheter of claim 9, wherein the array includes stiffening elements that produce a force biasing the array toward the undeployed configuration, and the frictional engagement between the elastomeric element and the surface of each wall is sufficient to prevent changes in the array caused by the biasing force.

11. The catheter of claim 9, wherein the deployment control mechanism further includes:
 a first rigid tube connected to the interior of the handle; and
 a second rigid tube connected to the rigid body distal of the first rigid tube and configured to be in a telescoping arrangement with the first rigid tube, wherein the deployment shaft extends through the first rigid tube and the second rigid tube.

12. The catheter of claim 9, wherein the walls extend from the first surface of the interior of the handle, and connect to a second surface of the interior of the handle opposite the first surface of the interior of the handle.

13. The catheter of claim 9, wherein the walls are parallel to each other and to the slot.

14. The catheter of claim 9, wherein the walls are symmetrically disposed on opposite sides of the slot.

15. The catheter of claim 9, wherein the array is continuously configurable between the undeployed configuration, a partially-deployed configuration, a nominally-deployed configuration, and the fully-deployed configuration.

16. The catheter of claim 15, wherein the gap formed between the walls at a distal end of the walls is greater than the gap at a proximal end, wherein the force applied to the knob sufficient to overcome the frictional engagement between the elastomeric element and the surface of each wall increases as the deployment control mechanism changes the array from the undeployed configuration, to the partially-deployed configuration, to the nominally-deployed configuration, and to the fully-deployed configuration.

17. The catheter of claim 15, wherein the gap formed between the walls is greater at a segment between a distal end of the walls and a proximal end of the walls, the segment corresponding to the nominally-deployed configuration, than at the distal end of the walls and the proximal end of the walls, wherein the force applied to the knob sufficient to overcome the frictional engagement between the elastomeric element and the surface of each wall decreases as the deployment control mechanism changes the array from the partially-deployed configuration to the nominally-deployed configuration, and increases as the deployment control mechanism changes the array from the nominally-deployed configuration to the fully-deployed configuration.

18. The catheter of claim 9, wherein the catheter is a cardiac mapping catheter and the array is an electrode array.

19. A catheter comprising:
 an elongate catheter body extending from a proximal end to a distal end;
 an array connected to the distal end of the catheter body, the array continuously configurable between an undeployed configuration, a partially-deployed configuration, a nominally-deployed configuration, and a fully-deployed configuration; and
 a handle connected to the proximal end of the catheter body, the handle including a slot extending along a portion of the handle between an interior of the handle and an exterior of the handle; and
 a deployment control mechanism including:
  a pair of walls projecting from a first surface of the interior of the handle, the walls disposed on opposite sides of the slot;
  a slider assembly including:
   a rigid body;
   an elastomeric element connected to the rigid body and at least partially disposed within a gap formed between the walls, wherein the elastomeric element frictionally engages with a surface of each wall;
   a tab connected to the rigid body and projecting from the rigid body and through the slot to the exterior of the handle;
   a knob connected to the tab at the exterior of the handle, wherein the knob is configured to maintain the elastomeric element within the gap between the walls; and
   a deployment shaft connecting the rigid body to the array, wherein a force applied to the knob sufficient to overcome the frictional engagement between the elastomeric element and the surface of each wall causes movement of the slider assembly and changes the configuration of the array,
  wherein the gap formed between the walls is greater at a segment between a distal end of the walls and a proximal end of the walls, the segment corresponding to the nominally-deployed configuration, than at the distal end of the walls and the proximal end of the walls, wherein the force applied to the knob sufficient to overcome the frictional engagement between the elastomeric element and the surface of each wall decreases as the deployment control mechanism changes the array from the partially-deployed configuration to the nominally-deployed configuration, and increases as the deployment control mechanism changes the array from the nominally-deployed configuration to the fully-deployed configuration.

20. The catheter of claim 19, wherein the array includes stiffening elements that produce a force biasing the array toward the undeployed configuration, and the frictional engagement between the elastomeric element and the surface of each wall is sufficient to prevent changes in the array caused by the biasing force.

* * * * *